United States Patent [19]

Gergely et al.

[11] Patent Number: 4,888,177

[45] Date of Patent: Dec. 19, 1989

[54] PHARAMACEUTICAL PREPARATIONS IN THE FORM OF INSTANT GRANULES OR TABLETS AND PROCESS FOR THEIR MANUFACTURE

[76] Inventors: Gerhard Gergely; Thomas Gergely; Irmgard Gergely, all of Gartengasse 8, A-1050 Vienna, Austria

[21] Appl. No.: 887,808

[22] PCT Filed: Nov. 2, 1985

[86] PCT No.: PCT/EP85/00585
§ 371 Date: Jul. 2, 1986
§ 102(e) Date: Jul. 2, 1986

[87] PCT Pub. No.: WO86/02834
PCT Pub. Date: May 22, 1986

[30] Foreign Application Priority Data

Nov. 5, 1984 [DE] Fed. Rep. of Germany ....... 3440288

[51] Int. Cl.$^4$ .......................... A61K 9/16; A61K 9/46
[52] U.S. Cl. .................................... 424/466; 424/470; 424/493; 424/494; 424/495; 424/496; 424/497
[58] Field of Search ............... 424/464, 466, 489, 470, 424/496, 497, 493, 494, 495

[56] References Cited

U.S. PATENT DOCUMENTS

| | | | |
|---|---|---|---|
| 3,780,195 | 12/1973 | Balassa | 424/493 X |
| 3,962,416 | 6/1976 | Katzen | 424/493 |
| 4,150,110 | 4/1979 | Yoshida et al. | 424/493 X |
| 4,177,254 | 12/1979 | Khan et al. | 424/361 X |
| 4,248,857 | 2/1981 | Deneale et al. | 424/493 |
| 4,309,405 | 1/1982 | Guley et al. | 424/493 |
| 4,459,280 | 7/1984 | Colliopoulos et al. | 424/493 |
| 4,501,726 | 2/1985 | Schröder et al. | 424/493 X |
| 4,542,011 | 9/1985 | Gleixner | 424/493 |
| 4,710,384 | 12/1987 | Rothman | 424/490 |
| 4,717,569 | 1/1988 | Harrison et al. | 424/494 |

FOREIGN PATENT DOCUMENTS

| | | |
|---|---|---|
| 368880 | 11/1982 | Australia . |
| 343477 | 5/1985 | Fed. Rep. of Germany . |
| 7638298 | 7/1976 | France . |
| 8414851 | 3/1985 | France . |
| 57-085316 | 5/1982 | Japan .................................. 424/493 |
| 58198417 | 11/1983 | Japan . |
| 5882067 | 2/1984 | Japan . |

OTHER PUBLICATIONS

Patent Abstracts of Japan, Section C, vol. 8, No. 34(C-210), (1471), 15 Feb. 1984, Tokoyo, (JP).

Primary Examiner—Thurman K. Page
Attorney, Agent, or Firm—Marmorek, Guttman & Rubenstein

[57] ABSTRACT

The invention relates to a pharmaceutical preparation that contains at least one pharmaceutically active substance at least one granular carrier material and a layer enveloping the carrier material that contains other components.

46 Claims, No Drawings

PHARMACEUTICAL PREPARATIONS IN THE FORM OF INSTANT GRANULES OR TABLETS AND PROCESS FOR THEIR MANUFACTURE

BACKGROUND OF THE INVENTION

The invention relates to a pharmaceutical preparation that contains at least one pharmaceutically active substance (excluding ibuprofen), especially an insoluble or a slowly or sparingly soluble active substance, at least one granular carrier material, and a layer enveloping the carrier material that contains other components.

In the manufacture of pharmaceutical preparations of solid active substances for oral administration, the active substance is usually mixed with flavor-improving filler materials and possibly coloring and/or aromatic substances. Various inactive ingredients such as protective colloids, disintegrating agents (hereinafter "disintegrants") and the like may also be added. If necessary, the preparation is granulated, reduced to the desired grain size, and then pressed into tablets. The tablets are than sugar-coated. Even with the best possible mixing action, in these tablets, the active substance is present in randomized form.

In recent times, it is increasingly becoming widespread to advise that many medicines be taken with a large amount of water, especially when the dosage to be administered is large, e.g., 1,000 mg of an active substance per administration. It is therefore often attempted to make the preparations in the form of instant powders or tablets, or in the form of effervescent powders or tablets, which prior to being administered are dissolved or suspended in water with or without formation of carbonic acid.

The absorption of active substances by the human body is a problem of distribution. If active substances that are present in small amounts are to be administered to the body optimally, then it is expedient to dilute such substances in advance or to dissolve them, since the surface of the active substance available for the absorption by the body is enlarged or better utilized. For example, ferrous gluconate, if it were not dissolved in water, would attack the mucous membrane of the stomach and cause side effects.

In the case of antibiotics, or of all water-insoluble substances, for example, in order to be absorbed more easily the substance should be suspended in water in the finest form.

In the manufacture of instant powders or tablets from insoluble or sparingly soluble active substances which are bitter tasting in water, the most diverse problems are encountered. On the one hand, due to the different grain sizes of the individual components of the mixture, it is often difficult to apportion the components precisely. On the other hand, when using freely soluble sugars (for the purpose of improving the flavor), the tablets decompose only very slowly in spite of the use of disintegrants because the concentrated sugar solution forming on the surface clogs the capillaries of the distintegrants, thereby disrupting or at least strongly retarding its effect.

SUMMARY AND DETAILED DESCRIPTION OF THE INVENTION

It is therefore the object of the present invention to devise a system that improves the manufacture of instant granulates or tablets such that problems of apportioning the individual components in manufacture are avoided, and such that the granulates or tablets disintegrate or dissolve in water at room temperature within 20 to a maximum 40 seconds. In the system of the present invention, the active substances are no longer present in randomized form, but are distributed and fixed in a controlled manner on the grain surface of a carbohydrate carrier material. The carrier is present preferably in a grain size of from 0.2 to 0.5 mm.

The pharmaceutical preparation according to the present invention enables a suspension in contact with water to be achieved nearly automatically, namely in that any colloids which may be present and the active substance are split off of the surface of the carbohydrate carrier grain with the aid of a disintegrant.

In particular, in the case of high dosages, the system is effective because a tablet that contains, e.g., half a gram or one gram of antibiotic must have a weight of at least 1 to 2 grams. A tablet of this dosage is difficult to swallow. When being administered it would also encounter absorption problems because in the stomach/digestive tract, an excessive local concentration of active substances would occur.

However, if the product is administered in instant form, i.e., suspended in water, then no distribution problems of any kind are encountered. The absorption also proceeds faster by virtue of the larger surface area, and in particular the product is considerably more pleasant to swallow. Children and elderly persons especially prefer a beverage to a tablet.

It has already been proposed (DE-OS 3434774) to apply micronized calcium carbonate to, e.g., citric acid crystals with the aid of an intermediate reaction layer of calcium citrate. In this reference, however, the problems sought to be overcome (provision of a sodium-free or low-sodium effervescent mixture) as well as the measures taken (reaction product of carrier and effervescent "active substance" as binding layer) are basically different from those proposed herein. A coating of carrier substance consisting of sparingly soluble colloids or pseudocolloids with active substances suspended in a solvent has also already been proposed (AT-PS 368,880); in this case too, other problems and measures are encountered than if a freely soluble carrier such as a sugar were to be first coated with a binding agent, and then the active substance precipitated on the binding agent.

It is known that soluble carbohydrates such as crystallized sugar, sorbitol, xylitol, melted mannitol, etc., can be used as a carrier. The carrier should be of as uniform size as possible. Its surface should be regular and may not contain any dust.

Up until the present time, instant granulates have had a pellet base. However, this has several disadvantages; it involves pelletizing, a basically unnecessary step that makes the manufacturing procedure more expensive and slower; it involves more binding agents than desired or necessary; pellets are—for this reason inter alia— more sparingly soluble than crystals; crystals or ground melted granulates have a more irregular and hence larger surface for anchoring active substances than the pellets, which by and large are nearly spherical.

According to the present invention, on the surface of every carrier grain, the active substance—and possibly also a disintegrant—are anchored, and that with or without the aid of a binding agent layer. Such a coating layer on every carrier grain contains, e.g., dextrin, polyvinyl-pyrrolidone or similar binding agents, and/or colloids such as alginates, xanthan gum, gelatins, maltodextrin or the like, and moreover has the effect, inter alia, of decelerating the dissolving of the sugar grain; then the micronized active substance is anchored on the still moist layer. If this is done with water only (and ethanol later on), then it is possible to anchor about 5 to 15%, especially about 10% by weight (relating to the carrier grain) of the micronized active substance (with or without a disintegrant) on the carrier grain surface. If it is desired to anchor 10 to 50%, especially as often desired about 20 to 30% by weight, the aforementioned binding agent layer is used.

The layer thickness of the binding agent produced on the carrier has a thickness of about 4 to 20 microns. However, such layers can be applied several times, so that layer thicknesses, especially on the simultaneous anchoring of larger amounts of active substances, of 50 to 200 microns around the carrier are possible.

Simultaneously or subsequently, a disintegrant can, as mentioned, also be applied, which on contact with water splits off the enveloping layer so that the active substances, with or without colloids, form a suspension. In this process, the sugar goes simultaneously or immediately thereafter into solution, so that at the end of the process, after 20–30 seconds of stirring with a spoon, a pleasantly tasting suspension of an active substance in water is obtained. As disintegrants, e.g., native starches such as corn starch, microcellulose, or cross-linked polyvinylpyrrolidone can be used in a known manner. It is important, naturally, for the binding agent layer—to the extent that a binding agent is used at all—to be as thin as possible, water-soluble or easily water-suspendible in order that the effect of the disintegrant in the water is not cancelled.

The structure can moreover contain buffers for increasing the stability of the active substance, coloring substances for making colored solutions, sweetening substances, etc. Further escort substances of this carrier system are aromatics and drying agents. Examples thereof are encapsuled aromatics that must also be present in the size of the end product, preferably 0.3 to 0.5 mm, in order that when being filled the mixture components are not separated, thereby assuring the product uniformity. Sodium sulfate and/or sodium carbonate in coarse-grained form can also be added in order to keep the system dry on packing and storing.

The process for making the pharmaceutical preparation comprises initially in removing under vacuum the air on the surface of the carrier to provide an intensive contact between the next following layer and the carrier. To this highly evacuated carrier a solvent, preferably with a binding agent, e.g., water with dextrin, polyvinylpyrrolidone, etc. is then applied; the carrier made from a carbohydrate is thereby partially dissolved at the surface so that a film forms on its surface that comprises a concentrated solution of the carrier with already integrated binding agent and/or colloid. Normally, the carrier mass must be heated up before, during and/or after the application of the surface layer by shell or direct heating in order that the solvent can more easily evaporate and a more adhesive—due to higher viscosity—higher concentration in the surface layer is obtained. The active substance components with simultaneous or subsequent addition of disintegrant is then applied to this adhesive surface.

After the layer is distributed uniformly on the carrier by corresponding technical measures, the product is dried by the application of vacuum. If the materials are sensitive to moisture, an additional heat treatment is preferably used to remove the residual moisture.

Only afterward can the aforementioned additives such as aromatics and drying agents be added. An absolutely uniform, free-flowing and easy-to-pack product is obtained. The use of known hydrophilic lubricants can naturally also be employed to obtain instant or eventually effervescent tablets.

However, the system according to the present invention need not be confined to water and/or ethanol only. If active substances that are water-sensitive are to be applied to the carrier, one can proceed as follows:

A mixture of fat and an emulsifier is melted and applied to the carrier—located preferably in an evacuated mixing drum—under heat treatment to the extent that the fat mixture does not solidify. This mixture will then distribute itself uniformly in the vacuum (due to the exclusion of air) and will have a layer of fat with emulsifier at the surface of the carrier. To this layer the water-sensitive active substance can be applied—as in the aforementioned manner eventually also together with a disintegrant—and distributed. In the case of slow solidification of the fat, the active substance is affixed on the carrier with the emulsifier by cooling and subsequent stirring.

The preparation according to the present invention is also suitable in an especially advantageous manner for making a mixture system with an effervescent effect. If it is desired to manufacture, e.g., a multivitamin mineral preparation in which the minerals could disrupt the stability of vitamins, the following procedure can be followed:

A carrier system is created that by means of an effervescent additive, preferably comprising calcium carbonate and/or sodium carbonate with citric acid, forms a carrier-effervescent system on the surface of the sugar crystals, or on the surface of, e.g., the citric acid crystal. In this system those minerals can be accommodated that are compatible with it, hence, e.g., ferrous salts, calcium salts, magnesium and the like.

It can be foreseen that for the effervescent mixture to contain citric acid and calcium carbonate, in which case the calcium carbonate envelops the citric acid, the adhesion being provided by a binding layer that is formed by incipient reaction of the calcium carbonate with the layer of the citric acid crystals that is near the surface.

In order to introduce the vitamins that in this procedure are sensitive, one proceeds as described above for the sugar or sorbitol carriers in that the vitamins are applied to carbohydrate carrier by means of a binding agent and disintegrant.

Since both systems can be created in the same particular dimensions (preferably 0.2 to 0.5 mm), they can be mixed together and do not separate when being filled into packets.

The existence of active substances consisting of acids that strongly irritate mucous membranes in the mouth and throat cavities, or that have strongly irritating acid residues is known. Such sparingly soluble to insoluble active substances include the profenes (generic name), usually propionoic acid or also benzene derivatives, of which derivatives with irritating action of different intensity are known. Under the designation profenes here, as below, all sparingly soluble to insoluble substances of similar structure—excluding ibuprofene—with acid residues etc. that strongly irritate mucous membranes in the aforementioned context are to be understood.

The profenes are active substances that have gained increasing significance for combating rheumatism and arthritis. They are usually insoluble in water, but have a very unpleasant taste. In particular, the mucous membranes of the esophagus are irritated itself by the composition and by the consistency of the product as well. It is also known from the literature that the profenes can cause gastrointestinal bleeding, as does acetylsalicylic acid, especially when the substances appear at the wall of the stomach in high concentration, whether in the form of a tablet or a capsule. It is hence of therapeutic advantage for these substances to be already suspended in water before being administered so that local over-concentrations in the gastrointestinal tract can no longer occur. However, for reasons of taste this suspension in water is not possible without additional measures because parts of the active substance remain behind in the mouth and in the esophagus, where they cause scratching and irritating taste sensations.

The invention also has the objective of providing a pharmaceutical preparation of the aforementioned type, as well as a process for the manufacture thereof, which eliminate the negative taste effects described above and which relieve the problems associated with the oral administration of medicines that as such irritate the mucous membranes.

This objective is fulfilled in that the particles of the mucous membrane irritating substance are coated with a layer of fumaric acid and at least one pseudocolloid, such as xanthan gum and/or maltodextrin. According to the present invention the coated particles are then applied to carrier grains of carbohydrate.

The process according to the present invention for making a pharmaceutical preparation of the type according to said invention is characterized in that the profene particles are covered in a vacuum mixing machine with a layer comprising at least one pseudocolloid and fumaric acid, and then vacuum dried.

It can especially be foreseen that the profene and the pseudocolloid or the pseudocolloids are first mixed with water in the vacuum mixing machine at a pressure of approx. 0.1 bar; and that after partial drying to approx. 0.2 bar, the fumaric acid is added, whereupon the product is dried completely.

The invention is based on the finding that the negative taste effect of existing profene preparations can be eliminated by covering the profene particles with at least one pseudocolloid and fumaric acid; in the simultaneous presence of fumaric acid, which has a low pH value, the negative taste effect is thereby prevented; the pseudocolloids merely perform the function of anchoring the water-insoluble profenes with the sparingly soluble fumaric acid. The manufacture of the pharmaceutical preparation according to the present invention and the process according to the present invention are expediently and advantageously performed by means of a vacuum mixing machine and by means of a process that are the subject of DE-OS 3434774.7, to which reference is made in full insofar as it serves as supplementary explanation of the ideas of the present invention.

EXAMPLE 1

80 parts of sugar of a grain size of 0.5 to 0.2 mm are suctioned with 1.5 parts of sodium cyclamate into a vacuum mixer preheated to 80° C. After the evacuation, a solution consisting of 70% ethyl alcohol and 2 to 3 parts of polyvinylpyrrolidone is suctioned into the vacuum mixer and mixed by oscillation for 3 minutes in order to wet the carrier grains contained therein. Then 11 parts of tryptophan are suctioned in, distributed for 5 minutes by oscillatory mixing and adhered to the surface of the carrier. Then the product is vacuum-dried down to the end value of 15 mbar, and then mixed with 0.6 parts of orange aromatic and 7 parts of citric acid, the grain size of about 0.5 to 0.3 mm of which should be near that of the enveloped carrier. This type of preparation is expedient especially for the high tryptophan doses often required.

EXAMPLE 2

For a multi-vitamin mineral effervescent granulate the two phases are manufactured separately.

(a) Manufacture of the effervescent phase containing minerals

In a vacuum mixing drum with a shell temperature of 80° C., 48 parts of crystallized citric acid, 6 parts of trisodium citrate, 2 parts of vitamin C, all with a grain size of 0.1 to 0.4 mm, as carrier, are suctioned with 0.6 part of saccharin and a mineral salt such as 0.6 part of ferrous gluconate, 0.01 part of sodium fluoride, and, if desired, coloring substances. The substances are heated up to 50° C. in the vacuum granulator while being mixed. Then a solution of 2 parts of pulverized citric acid in 0.7 part of water is made up and mixed with 1 part of ethanol. The heated-up mass is subjected to vacuum; then the solution is suctioned in and distributed on the carrier by oscillatory mixing for 5 minutes. 6 parts of precipitated calcium carbonate, 2 parts of magnesium oxide and 4 parts of sodium carbonate are then introduced, and the substances are distribute on the carrier by mixing for 2 to 5 minutes; then the mass is dried with vacuum for 20 minutes. Thereafter 9 parts of sodium carbonate and 2 parts of orange aromatic are mixed in, and the mass is discharged via a screening device.

(b) Manufacture of the vitamin phase 95 parts of crystallized sugar of a grain size of 0.1 to 0.4 mm are introduced into a preheated vacuum mixer and heated up to 40° C. Then the product is subjected to vacuum and the mass is wetted with a solution that in 1.4 parts of ethanol and 0.8 parts of methylene chloride contains 0.03 parts of a vitamin A palmitate, 0.3 parts of vitamin E acetate and 0.4 parts of polyvinylpyrrolidone. The desired mixture of solid vitamins is applied to the wetted sugar crystals by means of oscillatory stirring; then the solvents are dried off in vacuum.

Afterward, the two phases are mixed together in the desired ratio.

EXAMPLE 3

80 to 90 parts of crystallized sugar of a grain size of 0.6 to 0.2 mm are heated up in a vacuum mixer with shell heating to 80° C. Meanwhile, a melt of 3 parts of hardened castor oil and 0.1 to 0.2 part of an emulsifier (e.g., "Emulgin Bl" of Messrs. Henkel, acetylstearyl alcohol with a congealing range of between 32° and 37° C.) is prepared. The melt is introduced into the mixing drum and the shell is cooled down to a temperature of 60° C. Meanwhile, with oscillatory mixing the melt distributes on the surface of the sugar crystal grains. Then, while oscillatory mixing continues, 7 parts of amoxicillin trihydrate are added, the cooling is turned on and the shell is cooled down to a temperature of 30°

C., the mass cooling down to 65° C. and the melt solidifying. Mixing for the purpose of loosening 1 part of coconut aromatic is added and the mass is then discharged through a screening machine.

EXAMPLE 4

In accordance with the principles of the present invention, an active substance embedded in a matrix, in this case acelastine base, can be optimally suspended in a beverage. 92 parts of crystallized sugar of a grain size of 0.5 to 0.2 mm are introduced with 0.1 part of saccharin into a preheated vacuum mixer, and heated while being stirred to a temperature of 50° C. After the evacuation, a 50% sugar solution (solid substance 1.5 parts of sugar) is suctioned into the vacuum drum and distributed to the sugar crystals for 5 minutes. Then 0.3 parts of the active substance matrix that comprises 25 parts of shellac, 6 parts of Eudragite (a polymetacrylic acid ester of Messrs. Röhm Pharma) and 4 parts of acelastine base is introduced and adheres to the surface of the carrier. Then the surface is covered with 2 parts of each corn starch, maltodextrin and xanthan gum, and then dried while being stirred slowly down to an end value of 15 mbar. Then 1 part of lemon aromatic and 2 parts or sodium sulfate as drying agent that in grain size correspond to the carrier are added.

EXAMPLE 5

85 parts of instant sorbitol (spray-dried sorbite of a grain size of 0.4 to 0.1 mm) are suctioned into a vacuum mixer preheated to 70° C. A solution of 4 parts of liquid Karion (TM), in which the coloring substance is dissolved, is suctioned into the vacuum mixer and distributed for 5 minutes in order to wet the carrier contained therein. Then 5 parts of anhydrous ampicillin are introduced into the mixer and anchored to the surface of the carrier with oscillatory stirring. Then 1.5 part of karaya gum, 1.5 parts of carboxymethyl cellulose and 1 part of corn starch are applied to the still moist surface. Then while being stirred slowly, the product is dried under vacuum to an end value of 15 mbar. Finally, 0.1 parts of banana aromatic and 2 parts of sodium sulfate are added to the mass.

EXAMPLE 6

80 parts of melted mannitol that was subsequently ground to a grain size of 0.4 to 0.1 mm are heated up in a vacuum mixer with shell heating to 50° C. After the evacuation, a solution, consisting of 3 parts sugar, 3 parts water and 0.3 parts maltodextrin, is suctioned into the vacuum mixer and distributed on the carrier for 3 minutes by stirring. 7 parts of erythromycin succinate are suctioned into the vacuum mixer and distributed for 5 minutes to the carrier surface under oscillatory mixing. The active substance is so insoluble that on contact with water it jumps by itself out of the binding agent layer; hence, it can be processed without a distintegrating agent. Then 1.5 parts of maltodextrin and 1.5 parts of an alginate are applied to the carrier surface; then the product is dried, stirring slowly to an end value of 20 mbar vacuum. Stirring slowly, 0.1 parts of orange aromatic and 2 parts of sodium sulfate are then mixed in.

EXAMPLE 7

In a heatable vacuum mixer 40 parts of crystallized sugar, 2 parts of sodium phosphate, 6 parts of sodium citrate of similar grain size and the desired amount of sweetening substance are suctioned in and heated up during mixing to 50° C. Prior to the suctioning, a solution comprising 0.3 parts of dextrin, 3 parts of sugar, 1.5 parts of alcohol and 2 parts of water is mixed and the product is subjected to vacuum. The solution is then distributed to the carrier by mixing and then 14 parts of carbocistein are adhered to the wetted carrier surface. Thereafter 3 parts of dextrin, 3 parts of alginate, 0.6 parts of polyvinylpyrrolidone and 3 parts of corn starch are suctioned in, and the surface of the crystals are covered with it. The product is then vacuum dried, upon which common drying agents, aromatics, stabilizers and the remaining escort substances are mixed in.

EXAMPLE 8

200 parts of suprofene are treated with a solution of 10 parts of xanthan gum and 10 parts of maltodextrin in 50 parts of water; prior to the complete drying in vacuum at approximately 200 mbar, 20 parts of fumaric acid are added. After the complete drying a granulate is produced that is ground to a grain size of approximately 0.1 mm or smaller.

With the instant technology according to the present invention, these particles can be applied to crystallized sugar, 10 to 15 times the amount of sugar preferably being used and preferably enabling double the amount of citric acid to be added.

If such a mixture is made for individual doses of 200 mg of suprofene, with suitable aromatization a pleasant beverage is obtained that no longer exerts any sensations on the mucous membranes.

EXAMPLE 9

The same system as described above can be improved by the addition of an effervescent mixture of citric acid and calcium carbonate.

50 parts of citric acid are allowed to react in vacuum with 50 parts of calcium carbonate by the addition of 5 parts of 50% ethyl alcohol. This effervescent part is dried and added to the suprofene in 5 times the amount given in example 8.

A product thus manufactured exhibits a self-suspending effect of a slow effervescent mixture, the contained calcium ions apparently exerting a further improving effect on the taste of the suprofene.

EXAMPLE 10

3,000 parts of fine crystallized sugar are diluted with a solution of 60 parts of water and 40 parts of maltodextrin at 60° C.; in the vacuum mixing drum the solution is uniformly distributed to the crystallized sugar.

Then 200 parts of naproxene are distributed to the surface of the sugar and 20 parts of fumaric acid are applied. After the completed distribution thereof the product is dried to 50 mbar, and finely pulverized citric acid of a grain size of below 100 microns are introduced, with which the surface of the carrier is covered. Then the product is dried by vacuum to 10 mbar.

After the addition of desired amounts of sweetening substances and aromatics a uniform granulate is obtained that can be packed as individual doses of 200 to 400 mg naproxene in single packets.

We claim:
1. A pharmaceutical preparation, consisting essentially of
   a granulated carbohydrate carrrier material, and
   a coating layer adhering to each grain of said carrier material, said coating layer including at least one pharmaceutically active substance which is insoluble, sparingly soluble, or slowly soluble in water.

2. The pharmaceutical preparation of claim 1 wherein said carrier material comprises grains having a diameter in the range of 0.2 to 0.5 mm.

3. The pharmaceutical preparation of claim 1 wherein said pharmaceutically active substance comprises 5 to 15 percent by weight of said carrier material, said pharmaceutically active substance being embedded in the surface of each grain of carrier material.

4. The pharmaceutical preparation of claim 1 wherein said coating layer further consists essentially of a disintegrating agent.

5. The pharmaceutical preparation of claim 1 wherein said coating layer further consists essentially of a disintegrating agent selected from the group consisting of corn starch, microcellulose, and cross-linked polyvinylpyrrolidone.

6. The pharmaceutical preparation of claim 1 wherein said pharmaceutically active substance is a substance selected from the group of profenes.

7. The pharmaceutical preparation of claim 6 wherein said profene particles further consist essentially of a coating of fumaric acid and at least one hydro-colloidal material.

8. The pharmaceutical preparation of claim 7 wherein said hydro-colloidal material is selected from the group consisting of xanthan gum and maltodextrin.

9. The pharmaceutical preparation of claim 1 wherein said coating layer further consists essentially of a colloidal material.

10. The pharmaceutical preparation of claim 1 wherein said coating layer further consists essentially of an effervescent agent.

11. The pharmaceutical preparation of claim 1 wherein said coating layer further consists essentially of an effervescent agent comprising citric acid and calcium carbonate.

12. The pharmaceutical preparation of claim 1 wherein said pharmaceutically active substance is selected from the group consisting of ampicillin, erythromycin, and amoxicillin.

13. The pharmaceutical preparation of claim 1 wherein said pharmaceutically active substance is tryptophan.

14. The pharmaceutical preparation of claim 1 wherein said pharmaceutically active substance is selected from the group consisting of carbocistein, acelastine, and a vitamin.

15. A process for the manufacture of a pharmaceutical preparation, comprising
wetting a granulated carrier material consisting essentially of a carbohydrate with a solvent,
partially drying said granulated carrier material,
applying a coating layer consisting essentially of micronized particles of a pharmaceutically active substance thereby embedding said pharmaceutically active substance in said grain surfaces, and
drying said product.

16. The process of claim 15 wherein said granulated carrier material is wetted under vacuum.

17. The process of claim 15 wherein said solvent is water.

18. The process of claim 15 wherein said solvent is ethanol.

19. The process of claim 15 wherein said product is dried under vacuum.

20. The process of claim 15 further consisting essentially of adding a substance to said solvent, said substance being selected from a group consisting of a low weight alcohol, a protection colloid, a coloring substance, and an aromatic compound.

21. The process of claim 15 further consisting essentially of theating said carrier material under vacuum, adding a melt of an ester of a fatty acid containing an emulsifying agent, partially cooling said product, thereupon adding said active substance, and coating said final product.

22. A pharmaceutical preparation, comprising
a granulated carbohydrate carrier material, and
a coating layer adhering to each grain of said carrier material, said coating layer including at least one pharmaceutically active substance which is insoluble, sparingly soluble, or slowly soluble in water, said pharmaceutically active substance being covered with a coating of fumaric acid.

23. The pharmaceutical preparation of claim 22 wherein said pharmaceutically active substance is further coated with a hydro-colloidal material.

24. The pharmaceutical preparation of claim 22 wherein said coating layer further comprises a disintegrating agent selected from the group consisting of corn starch, microcellulose, and cross-linked polyvinylpyrrolidone.

25. The pharmaceutical preparation of claim 22 wherein said pharmaceutically active substance is a substance selected from the group of profenes.

26. The pharmaceutical preparation of claim 23 wherein said hydro-colloidal material is selected from the group consisting of xanthan gum and maltodextrin.

27. The pharmaceutical preparation of claim 22 wherein said coating layer further comprises a colloidal material.

28. The pharmaceutical preparation of claim 22 wherein said pharmaceutically active substance is selected from the group consisting of carbocistein, acelastine, a vitamin, tryptophan, amoxicillin trihydrate, acelastine, ampicilin, erythromycin succinate, carbocistein, suprofene, naproxene, and combinations thereof.

29. A pharmaceutical preparation comprising
a granulated carbohydrate carrier material, each grain of said carbohydrate material being a single crystal,
a first coating layer adhering to each grain of said carrier material, said coating layer comprising a binding agent, and a second coating layer on top of and adhering to said first coating layer, said second coating layer comprising at least one pharmaceutically active substance which is insoluble, sparingly soluble, or slowly soluble in water, said pharmaceutically active substance comprising 20 percent or more by weight of said carrier material.

30. The pharmaceutical preparation of claim 29 wherein said pharmaceutically active substance comprises 20 to 30 percent by weight of said carrier material.

31. The pharmaceutical preparation of claim 30 wherein said binding agent is selected from the group consisting of dextrin and polyvinylpyrrolidone.

32. The pharmaceutical preparation of claim 30 wherein said first coating layer further comprises a disintegrating agent.

33. The pharmaceutical preparation of claim 32 wherein said disintegrating agent is selected from the group consisting of corn starch, microcellulose, and cross-linked polyvinylpyrrolidone.

34. The pharmaceutical preparation of claim 30 wherein said active substance is selected from the group of profenes.

35. The pharmaceutical preparation of claim 34 wherein said active substance is covered with a coating of fumaric acid and at least one hydro-colloidal material.

36. The pharmaceutical preparation of claim 35 wherein said hydro-colloidal material is xanthan gum or maltodextrin.

37. The pharmaceutical preparation of claim 30 wherein said first coating layer further comprises a colloidal material.

38. The pharmaceutical preparation of claim 30 wherein said first coating layer further comprises an effervescent agent.

39. The pharmaceutical preparation of claim 38 wherein said effervescent agent comprises citric acid and calcium carbonate.

40. The pharmaceutical preparation of claim 30 wherein said binding agent comprises an ester of a fatty acid and an emulsifying agent.

41. The pharmaceutical preparation of claim 40 wherein said ester of a fatty acid comprises hardened castor oil.

42. The pharmaceutical preparation of claim 41 wherein said pharmaceutically active substance is amoxicillin trihydrate.

43. The pharmaceutical preparation of claim 30 wherein said pharmaceutically active substance is selected from the group consisting of ampicillin, erythromycin, and amoxicillin.

44. The pharmaceutical preparation of claim 30 wherein said pharmaceutically active substance is tryptophan.

45. The pharmaceutical preparation of claim 30 wherein said pharmaceutically active substance is selected from the group consisting of carbocistein, acelastine, and a vitamin.

46. A process for the manufacture of a pharmaceutical preparation, comprising
wetting a granulated carbohydrate carrier material with a solvent, each grain of said carbohydrate material being a single crystal, said solvent containing a binding agent,
partially drying said granulated carrier material to thereby adhere a first coating layer comprising a binding agent to each grain of said carrier material,
applying a second coating layer containing micronized particles of a pharmaceutically active substance on top of and adhering to said first coating layer, and
drying said product.

* * * * *